United States Patent [19]
Lightman et al.

[11] Patent Number: 5,810,828
[45] Date of Patent: Sep. 22, 1998

[54] ADJUSTABLE DEPTH DRILL GUIDE

[75] Inventors: David A. Lightman, Davie; Thomas J. Mickel, Jupiter, both of Fla.

[73] Assignee: Mednext, Inc., West Palm, Fla.

[21] Appl. No.: 800,267

[22] Filed: Feb. 13, 1997

[51] Int. Cl.[6] .................................................. A61B 17/56
[52] U.S. Cl. .............................................. 606/80; 606/96
[58] Field of Search .................................. 606/80, 79, 81, 606/82, 83, 84, 85, 96, 97, 98, 102; 408/113, 202, 203, 241 S

[56] References Cited

U.S. PATENT DOCUMENTS

| | | |
|---|---|---|
| 3,628,522 | 12/1971 | Kato . |
| 3,682,177 | 8/1972 | Ames et al. . |
| 4,019,827 | 4/1977 | Christianson et al. . |
| 4,273,117 | 6/1981 | Neuhauser . |
| 4,516,575 | 5/1985 | Gerhard et al. . |
| 4,647,260 | 3/1987 | O'Hara et al. . |
| 4,710,075 | 12/1987 | Davison ..................................... 606/96 |
| 4,830,001 | 5/1989 | Walus . |
| 4,931,056 | 6/1990 | Ghajar et al. . |
| 5,192,293 | 3/1993 | Cartwright et al. . |
| 5,207,681 | 5/1993 | Ghadjar et al. . |
| 5,304,191 | 4/1994 | Gosselin . |
| 5,380,132 | 1/1995 | Parks . |
| 5,382,250 | 1/1995 | Kraus . |
| 5,409,493 | 4/1995 | Greenberg . |
| 5,439,005 | 8/1995 | Vaughn . |
| 5,520,692 | 5/1996 | Ferrante ..................................... 606/80 |
| 5,536,271 | 7/1996 | Daly et al. ................................ 606/80 |
| 5,540,694 | 7/1996 | DeCarlo, Jr. et al. .................... 606/80 |
| 5,575,793 | 11/1996 | Carls et al. ................................ 606/80 |

OTHER PUBLICATIONS

*The Midas Rex Micro–Mini Drill Guide*, Midas Rex Pneumatic Tools, Inc., 3001 Race Street, Fort Worth, TX 76111–4117 (2 pages). Date unknown.

*Primary Examiner*—Guy V. Tucker
*Attorney, Agent, or Firm*—Woodard, Emhardt, Naughton Moriarty & McNett

[57] ABSTRACT

An adjustable guide for a rotary tool shaft adapted to penetrate a work-piece, the tool shaft connected to a motor having a housing. The adjustable guide including a base connected to the housing and the base having a series of threads. A stop is threadedly engaged with the threads of the base and axially adjustable with respect to the base by rotational movement about the base. A guide tube is slidably connected to the base and is limited in its movement by engagement with the stop. An indexed locking mechanism interengages the base and the stop to lockingly prevent rotation of the stop about the base at pre-set intervals, thereby axially displacing the stop a preset discrete distance between each indexed interval. The stop controlling axial displacement of the guide tube and thereby controlling the depth of penetration of the rotary tool shaft into the work-piece.

23 Claims, 6 Drawing Sheets

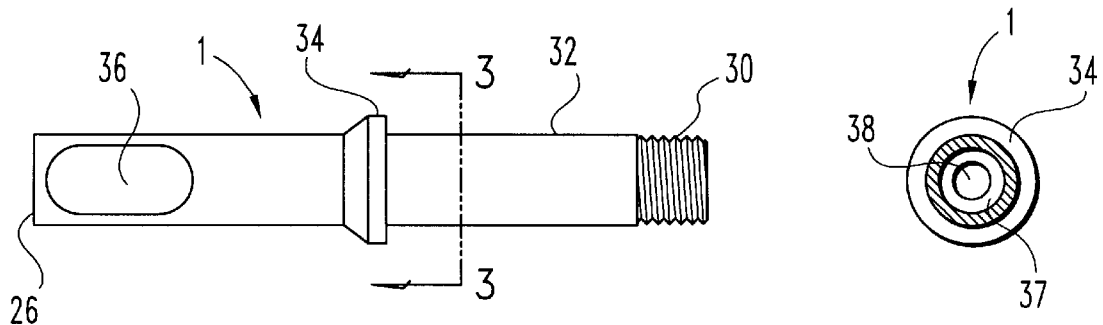
Fig. 2(a)　　　　Fig. 3
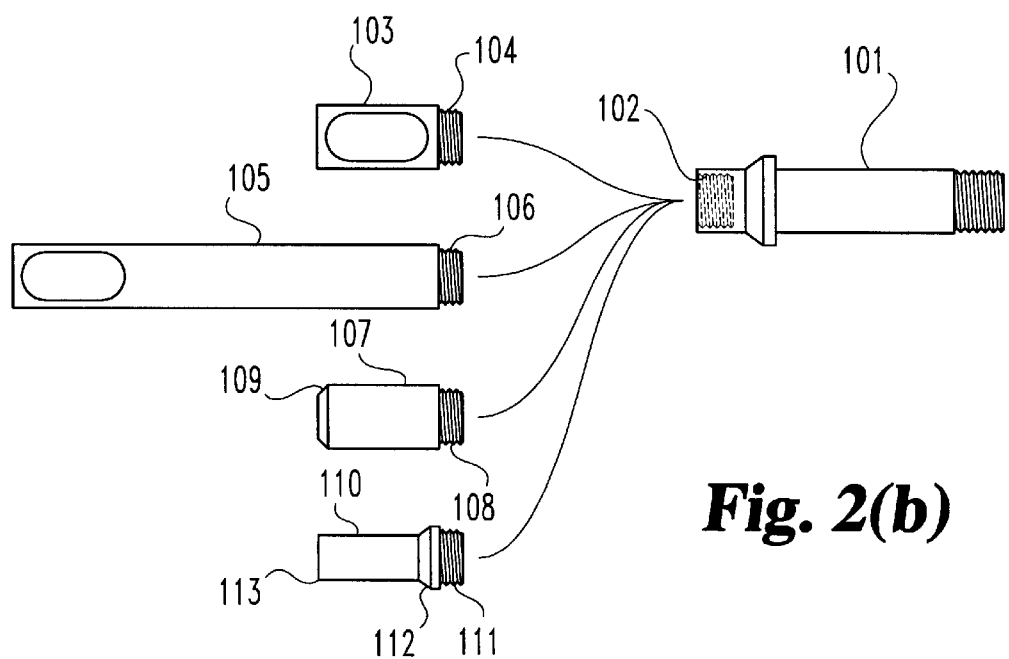
Fig. 2(b)

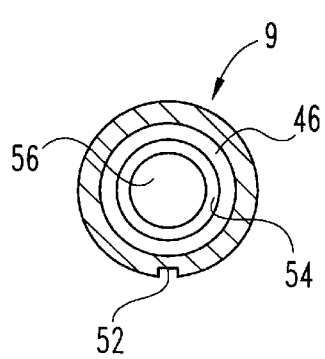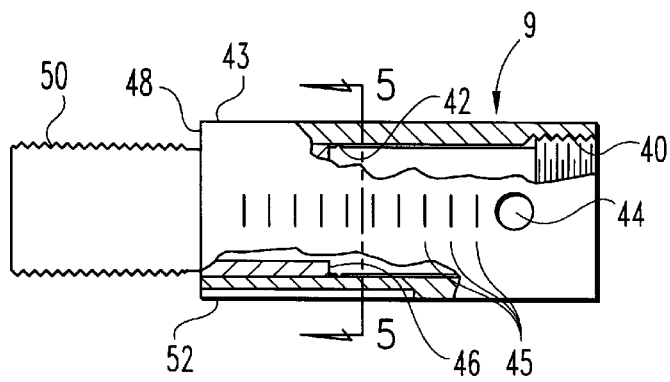
Fig. 5     Fig. 4
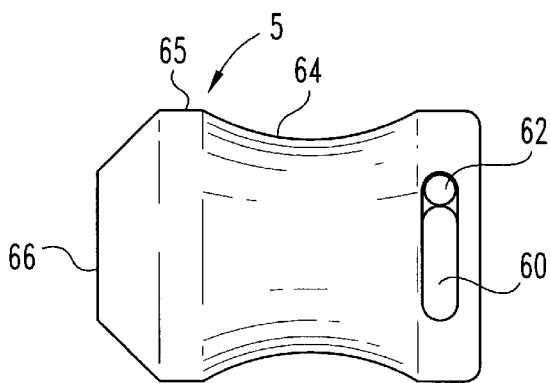
Fig. 6
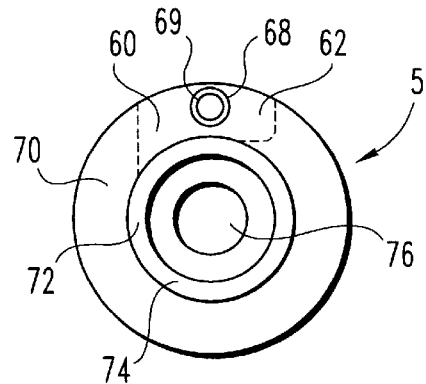
Fig. 7

ADJUSTABLE DEPTH DRILL GUIDE

BACKGROUND OF THE INVENTION

The present invention relates broadly to guides for surgical instruments with rotational shafts having operable bits adapted for cutting, drilling or similar procedures on a patient. More specifically, the present invention relates to adjustable depth guides for use in surgical applications requiring precision depth adjustment that may be lockingly maintained at the desired depth.

Surgical guides of various types have long been employed in the medical arts. Drill guides, for example, are particularly useful in preparing long bones and joint sites for implants such as hip and knee prostheses and various spinal fixation devices. Such applications require precise depth control of the drill bit penetration to ensure the site is properly prepared so that the implant is securely seated and the surrounding tissue is not damaged in the process. Moreover, as is common in many degenerative and trama-induced spinal surgeries, it is desirable to fuse adjacent vertebrae or other bone to itself or to the implant. For the purposes of promoting such fusion, it is desirable to remove a predetermined thickness of cortical bone to expose the underlying cancellous bone. In this procedure it is often necessary that the cutting bit or burr extend only a predetermined distance into the working surface.

Other surgical procedures that also require precise control over drill bit penetration include maxillofacial and cranial surgeries. Generally, the treatment of fractures of the craniomaxillofacial region proceeds by reducing the fractured bones to their anatomically correct positions, and thereafter fixing the bones in place. The bones may be fixed in place either by interosseous wire or by the technique of mini-plate fixation. In either case, holes must be drilled in the bone structure for receiving the interosseous wire or screws for holding the mini-plates to the bone.

As with spinal surgery, in the drilling of holes into such bone structure, great care must be taken to ensure that the holes are drilled at precisely the correct place and to precisely the correct depth. This is complicated because visual assessment of the process as it proceeds is typically not possible. If the holes are not drilled at the correct location, strain may be transmitted by screws to the surrounding bone structure. This may cause the bone to resorb in the vicinity of the screws, with the resulting loosening of the hardware.

In performing a craniotomy, i.e., opening the skull for access to the brain, a series of holes must first be formed at the corners of the section of skull to be removed. A danger present in such craniotomies is the risk of penetration too far into the skull while creating such holes, possibly even piercing the dura, i.e., the membrane protecting the brain, and the underlying brain tissue itself. Obviously, if the dura and/or the brain underlying it are penetrated, very serious damage can occur.

In view of this danger, surgeons have long been aware of the importance of perforating a patient's cranium at an angle of substantially 90° to prevent damage to underlying tissue by a partially protruding drill bit. Consequently, as disclosed in U.S. Pat. No. 4,931,056, surgical drill guides have been provided with a tripod base to orient the drill bit at a 90° angle with respect to a plane tangent to the surface of the skull at the drill site. Further, as disclosed in U.S. Pat. Nos. 4,830,001 and 5,207,681, surgical drill guides for use in cranial surgery have been provided with a clutch mechanism that disengages when the bit projects through the bone structure. An alternative approach to these clutch mechanisms is disclosed in U.S. Pat. No. 5,382,250. This approach employs a series of spacer rings placed around the drill bit to prevent over penetration. While such guides can be used to perform some specific surgical procedures, they lack the ability to conveniently and accurately provide adjustable depth of the drill bit in a blind procedure. Moreover, reliance on a clutch type drill guide stop is not suitable for applications where the drill bit is not intended to extend through the entire bone.

Several types of guides have sought to provide this depth adjustment through a mechanical mechanism. In U.S. Pat. No. 3,682,177, an indexed guide tube is shown which is slidable to a desired depth. To prevent the tube from sliding during operation, a nut surrounding a chuck must be rotated until it forces the chuck to securely hold the slidable guide tube. Similarly, in U.S. Pat. No. 5,439,005 a telescoping guide tube is only extendable once a threaded collar has been loosened by rotational movement. After loosening, the guide tube may be extended or retracted by manual manipulation and then secured in the desired position by retightening the threaded collar.

Another alternative configuration is utilized by the Midas Rex DG1 and DG2 Micro-Mini drill guides shown in product sheets submitted with this application. These guides have a base section which can be attached to a motor housing, a stop threadedly coupled to this base, and a guide slidable through the stop and spring-biased to fully extend. The guide includes an external shoulder engagable with the stop to prevent further movement of the guide into the stop, thereby preventing further penetration of the drill bit into the work-piece. The guide tube itself has a tapered tip corresponding to chamfered openings in a companion series of plating systems. Because of the reduced inner diameter of the guide as a result of this taper, the Midas Rex adjustable guides may be used only with a limited size of drill bits. In fact, for the Midas Rex device, this limitation necessitates the offering of two different guides to accommodate the desired drill diameters. Moreover, the tapered tip inhibits very precise depth measurements when used with other plate systems, since it is difficult to determine how far the taper of the tip extends into the plate opening. Thus, unless the user determines the exact depth that the tapered tip extends into the plate, the drill bit depth adjustment will necessarily be off by a fraction of the plate thickness.

As with the previously discussed systems, a collar (or in the case of the Midas Rex Micro-Mini drill guides, a lock nut), must first be loosened by rotational movement before adjustment of the guide tube depth can be performed. Loosening of these locking mechanisms requires several finger strokes or possibly a tool to rotate the nut away from the engaging surface. Further, with the Midas Rex guides the final tightening of the lock nut against the base tends to rotate the stop slightly, thereby altering the precise depth setting. To prevent this from occurring, the user must firmly hold the stop in the desired position until the lock nut is securely tightened. Moreover, since the locking mechanism relies on rotational force and the shaft within the guide transmits rotational force, there is a possibility of accidental loosening of the locking mechanism and subsequent movement of the guide tube. Although transmission of rotational force to the guide can be a problem, a greater problem is encountered as a result of vibrations generated during use of the drills which, over time, can loosen the locking collar. Furthermore, the prior art devices provide adjustment of the guide over a continuous range, thus relying on the user to accurately set a depth using an additional measuring device each time the mechanism is adjusted.

A need therefore exists for a locking mechanism that does not utilize rotational movement to release the adjustment mechanism. Moreover, the locking mechanism should be cooperable with the adjustment mechanism to provide indexed depth adjustment of the guide tube for precise adjustment in predetermined discrete increments. Furthermore, index markings on the adjustment mechanism should be provided to visually indicated the depth the drill bit will plunge into the work-piece.

SUMMARY OF THE INVENTION

One form of the present invention contemplates an adjustable guide for a rotary tool shaft adapted to penetrate a depth into a work-piece, the rotary tool shaft connected to a motor, the motor having a housing, the guide comprising a base having a first series of threads with a pitch, the base connected to the housing, a stop having a second series of threads threadedly engaging the first series of threads, wherein rotation of the stop about the base produces an axial displacement proportional to the pitch, a latch engagable with the base and the stop, the latch having an actuator controlling the latch between a latched position preventing rotation of the stop with respect to the base and an unlatched position permitting rotation of the stop with respect to the base, and a guide tube having a longitudinal channel for receiving the rotary tool shaft, the guide tube slidably connected to the base, whereby rotation of said stop about said base changes the depth of penetration of the rotary tool shaft into the work-piece.

Another form of the invention contemplates an adjustable guide for a rotary tool shaft adapted to penetrate a depth into a work-piece, the rotary tool shaft connected to a motor, the motor having a housing, the guide comprising a base having a first series of threads having a pitch, the base connected to the housing, a stop having a second series of threads, the second series of threads threadedly engaging the first series of threads, wherein rotation of the stop about the base produces an axial displacement proportional to the pitch, an indexed locking mechanism engagable with the stop and the base, the indexed locking mechanism operable by non-rotational movement to lock rotation of the stop about the base at pre-set intervals to thereby produce a pre-determined axial displacement of the stop from said base, and a guide tube having a longitudinal channel for receiving the rotary tool shaft, the guide tube slidably connected to the base, whereby rotation of said stop about said base changes the depth of penetration of the rotary tool shaft into the work-piece.

Still another form of the invention contemplates an adjustable guide for a rotary tool shaft adapted to penetrate a depth into a work-piece, the rotary tool shaft connected to a motor, the motor having a housing, the guide comprising a base connected to the housing, the base having an external surface with a distal end including a series of external threads having a pitch, the external surface defining at least one axial groove, a stop having an inner surface defining a series of internal threads, the internal threads threadedly engaging the external threads, wherein rotation of the stop about the base produces an axial displacement proportional to the pitch, a latch pivotally attached to the stop, the latch having a projection adapted to engage the groove, wherein engagement of the projection in the axial groove prevents rotation of the stop about the base, and a guide tube having a longitudinal channel for receiving the rotary tool shaft, the guide tube slidably connected to the base, whereby rotation of said stop about said base changes the depth of penetration of the rotary tool shaft into the work-piece.

Additionally, the invention includes a method for adjusting a drill guide disposed about a drill bit interconnected with a motorized hand-piece, comprising the steps of providing an adjustable depth guide having a base with index markings, a stop threadedly received about the base, and an indexed locking mechanism having an actuator operable by non-rotational movement to prevent rotation between the base and the stop and thereby prevent axial displacement, positioning the adjustable depth guide over the drill bit, attaching the base to the motorized hand-piece, depressing the actuator of the indexed locking mechanism to unlock the locking mechanism, rotating the stop about the base until the desired index marking is adjacent the stop, releasing the actuator, rotating of the stop until the indexed locking mechanism engages with the desired index marking adjacent the stop, thereby setting the guide to stop at a predetermined depth.

An object of the present invention is to provide an indexed locking mechanism for an adjustable depth guide. The locking mechanism locking rotation of the adjustment means at a series of pre-set intervals thereby adjusting the drill bit penetration by a discrete unit.

A further object of the present invention is to provide index markings on the adjustment mechanism. The index markings provide a visual indication of the number of revolutions of the stop about the base and provide the user with an indication of the maximum extent of drill bit penetration into a work-piece.

Still a further object of the present invention is the provision of a latch mechanism operable by non-rotational force.

Another object of the present invention is to provide a guide tube having a substantially uniform outer diameter adjacent the distal tip and a flat surface on the distal tip. This configuration aids in precisely setting the plunge depth of the drill bit by preventing the guide tube from partially extending into a chamfered screw opening in a plate. Thus the user only needs to determine the desired plunge depth into the work-piece and then add the thickness of the plate.

An additional object of the present invention is to provide a guide tube with removably attached guide tube tips.

Related objects and advantages of the present invention will be apparent from the following description.

BRIEF DESCRIPTION OF THE DRAWINGS

FIG. 2(a) is a side view of the drill guide tube of FIG. 1.

FIG. 2(b) is a side view of an alternative drill guide tube having interchangeable tips.

FIG. 3 is a cross-sectional view taken along section lines 3—3 of the guide tube of FIG. 1.

FIG. 4 is a partial cross-sectional view of a guide base of FIG. 1.

FIG. 5 is a cross-sectional view taken along section lines 5—5 of the drill guide base of FIG. 4.

FIG. 6 is a side view of the guide stop of FIG. 1.

FIG. 7 is an end view of the guide stop of FIG. 6.

DESCRIPTION OF THE PREFERRED EMBODIMENTS

Figure 1A:
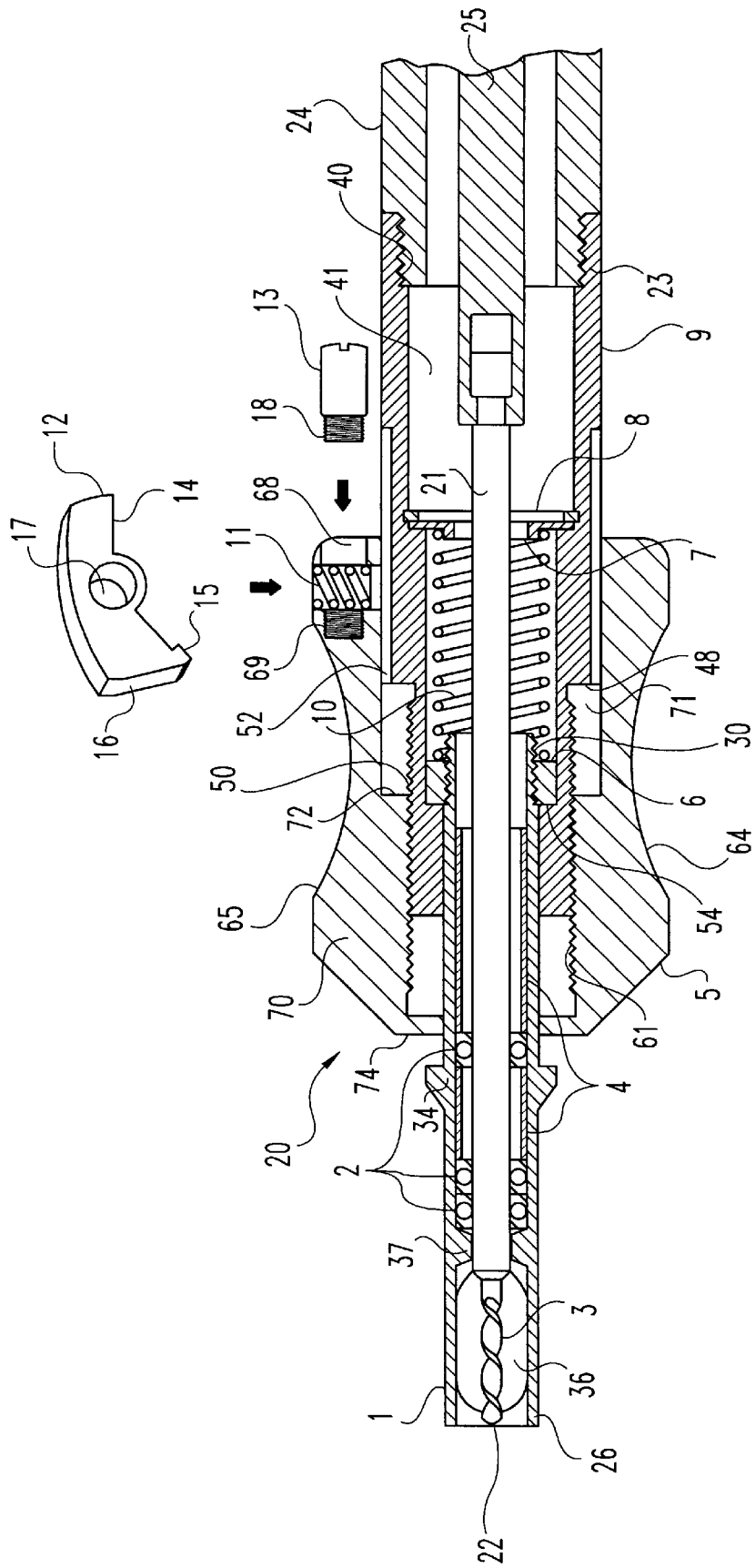
FIG. 1(a) is a cross-sectional view of the adjustable depth drill guide according to the present invention with the drill bit disposed within the guide tube.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Surgical drill guides of various types are well known in the art. However, the present invention presents a unique and non-obvious adjustable depth drill guide providing both accuracy in depth selection and ease of use. Referring now to FIG. 1, the adjustable depth drill guide 20 includes guide base 9, adjustable stop 5, indexed latching mechanism comprised of latch 12 and axial groove 52 disposed on base 9, and retractable guide tube 1. These components are cooperable to provide an adjustable depth drill guide having predetermined indexed latching positions for precise and convenient depth control.

Referring now to FIGS. 1, 4 and 5, base 9 has end 23 adjacent motor housing 24 and threadedly engaged with the housing by internal threads 40. Base 9 further defines a cavity 41 adapted to receive a drill bit and a portion of the motor housing and chuck assembly 25 (shown diagrammatically). The end of guide base 9 opposite end 23 defines a series of external threads 50 of reduced outer diameter. Disposed between these two ends and the differing diameters is an external shoulder 48. Extending between shoulder 48 and end 23 is a substantially smooth cylindrical surface 43. Defined within surface 43 is axial groove 52. In the preferred embodiment axial groove 52 has a substantially rectangular cross-section; however, it is contemplated that the groove could have any type of cross section provided to cooperate with a corresponding latch projection. On the internal surface defining cavity 41, there is defined a circumferential internal groove 42, a first protruding shoulder 46 and a second protruding shoulder 54.

Referring now to FIGS. 1, 6 and 7, guide stop 5 defines an internal channel 71 having a longitudinal axis and adapted to receive guide base 9. Channel 71 is further defined by internally protruding shoulder 72 and a series of internal threads 61 cooperable with external threads 50 on guide base 9. Guide stop 5 further includes internal flange 74 defining guide tube channel 76 and terminating channel 71. Machined out of guide stop sidewall 70 is an oblong slot 60 extending through the sidewall, thereby creating a passage into channel 71. Further machined into sidewall 70 adjacent oblong slot 60 is circular recess 62. Above oblong slot 60, sidewall 70 defines an axially aligned smooth bore opening 68 having an offset axis parallel to the axis of channel 71. Extending below oblong slot 60 is a smaller diameter internally threaded opening 69 axially aligned with opening 68.

Oblong slot 60 is adapted to receive latch 12 with engagement end 16 passable through the oblong slot into channel 71. Latch 12 is pivotally connected to stop 5 by pivot pin 13 extending through opening 17 in the latch. Pivot pin is held in place by extending through opening 68 in stop 5 with externally threaded portion 18 being threadedly engaged by internally threaded opening 69. Latch 12 is spring biased by spring 11 positioned in recess 62 to a normally locked position with engagement end 16 extending through slot 60 and into cavity 71. Engagement end 16 further defines projection 15 having a substantially rectangular cross-section corresponding to the rectangular cross-section of axial groove 52 and cooperable therewith to prevent rotation of guide stop 5 with respect to guide base 9. It being understood that the latch may be actuated to an unlocked position by applying pressure to actuator 14 of latch 12 to overcome the spring force of spring 11 and thereby withdraw projection 15 from axial groove 52. With projection 15 withdrawn from axial groove 52, guide stop 5 is free to rotate with respect to guide base 9. Furthermore, with actuator 14 released, guide stop 5 may continue to rotate about base 9 until projection 15 engages axial groove 52.

Guide tube 1 is illustrated in FIGS. 1 through 3. Guide tube 1 has external threads 30 disposed on one end and sight window 36 disposed on the opposite end. Disposed between these two features is externally projecting circumferential shoulder 34, it being understood that shoulder 34 may abuttingly engage flange 74 of guide stop 5 to prevent further axial movement of guide tube 1 into base 9. Disposed between shoulder 34 and threads 30 is a substantially smooth cylindrical portion 32. Guide tube 1 defines an internal channel 38 adapted to receive a series of bearings and spacers, as well as drill bit 3. The area for receiving bearings and spacers is defined at one end by internal flange 37. Preferably the preferred embodiment, the internal diameter of the guide tube adjacent sight window 36 is large enough to receive a cutting tip larger in diameter than the shaft of the cutting tip.

In the preferred embodiment, guide tube 1 has a non-tapered tip 26 having a substantially flat end which abutting engages the work surface or the surface of a plate. This is particularly useful when drilling holes in the bone for screw placement through a fixation plate with pre-drilled chamfered holes. The flat end of the guide tube prevents the guide tube from partially extending into the pre-drilled holes in the fixation plate. Thus, the surgeon may accurately adjust the drill guide by taking into account the entire thickness of the plate. Moreover, unlike guides with tapered tips, the guide tube of the present invention may be used with a wide variety of drill bit diameters.

In addition to facilitating accurate setting of the depth of drill bit penetration for a variety of plate configurations, the flat end of guide tube 1 may serve as an alignment guide for forming holes in the cranium. For cranial penetration, it is desirable to drill at a substantially perpendicular angle to the surface of the bone being penetrated. With the present invention, in many situations, flat tip 26 of the guide tube 1 will uniformly engage the spherical surface of the cranium, thereby indicating to the user that the drill bit is perpendicular to the surface.

The preferred embodiment shows guide tube 1 with an integral tip; however, it is contemplated that the tip of the guide tube may be removable. FIG. 2(b) shows an alternative embodiment for a guide tube cooperable with the present invention. Guide tube 101 has an internally threaded distal end 102 (threads shown in dashed lines) adapted to receive a variety of tip attachments. Although other configurations are possible, exemplary attachments are shown. Each attachment tip 103, 105, 107, and 110 have externally threaded attachment ends 104, 106, 108, and 11, respectively. These guide tube attachment tips may be removably mounted on guide tube 101 to perform a variety of functions.

Attachment tips 103 and 105 provide the guide tube with the flat tip as previously discussed; however, the length of the guide tube may be changed by addition of the tips. Attachment tip 107 has a tapered tip 109 which can be particularly useful with, among other things, plates having corresponding chamfered openings. Attachment tip 110 has a tapered shoulder 112 disposed between flat tip 113 and attachment end 111. While this tip can be used in many applications, one specific use is for the shoulder to engage a template while a cutting burr reproduces the desired pattern at a set distance from the template. Although FIG. 2(b) shows the various tips as being removable, it is contemplated and within the spirit of the invention that the tip could be integrally formed with the guide tube and that the guide tube could be removable from the adjustment assembly.

Figure 8:
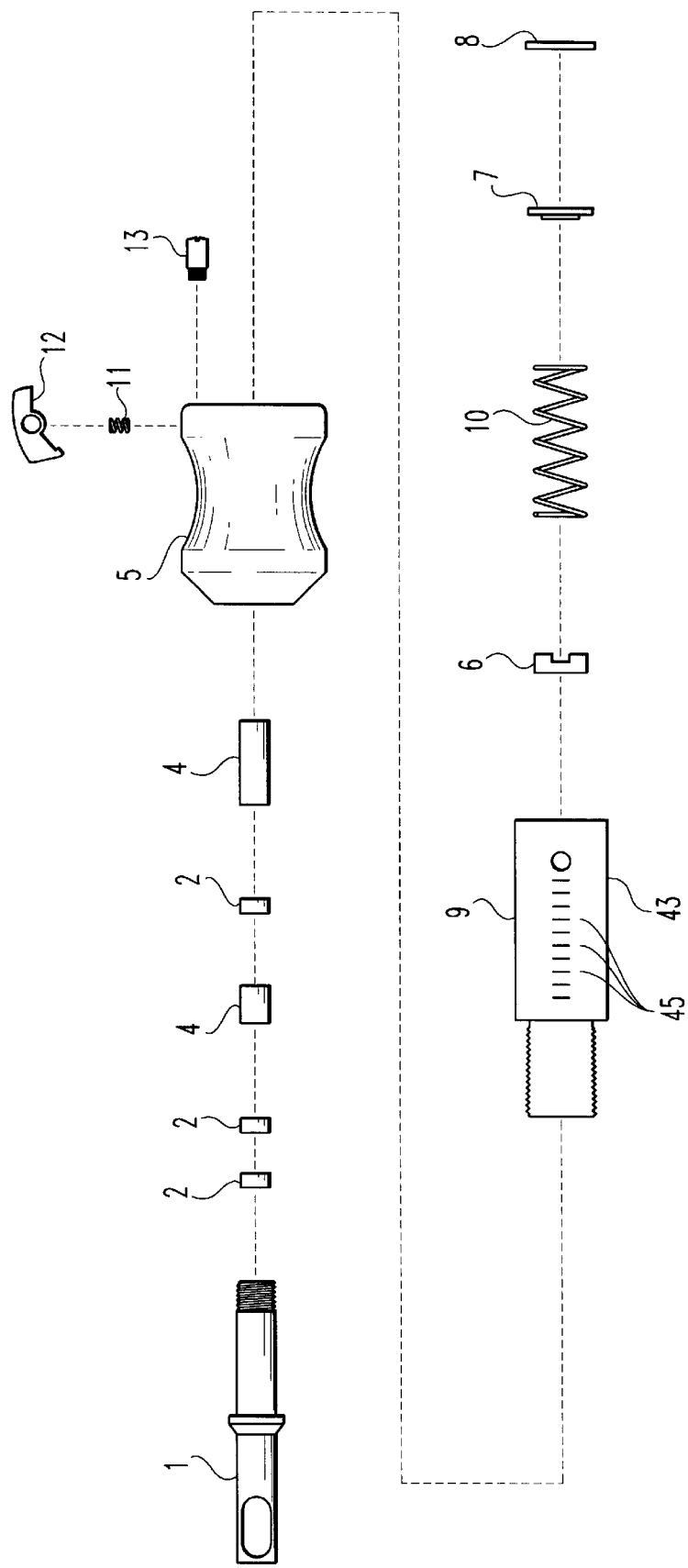
FIG. 8 is an exploded view of the adjustable depth drill guide of FIG. 1.

Referring now to FIG. 8, an exploded view of the components according to the present invention, these components may be assembled into the apparatus as shown in FIG. 1. Bearings 2 and bearing spacers 4 are inserted into the internal channel of guide tube 1. Preferably, bearing spacers are held in place by an adhesive compound. Although an adhesive compound is used in the preferred embodiment, it is understood that alternative fixation means are contemplated. Bearings 2 radially support the rotary shaft of twist drill bit 3 while it rotates and allow it to move axially relative to guide tube 1.

Referring now to the assembly of guide stop 5, latch spring 11 is placed in recess 62 defined in the outer wall 70 of guide stop 5. Latch 12 is then inserted into slot 60 with actuator 14 adjacent latch spring 11 and engagement end extending through slot 60. Latch 12 is held in place by pivot pin 13 extending through opening 17. Pin 13 is securely held in place by the threaded engagement of threads 18 with internally threaded opening 69. Preferably, the threads 18 of the pin are coated with a commercially available thread locking compound (Lok-Tite markets such a product) to fix the pin in threaded opening 69. This attachment permits latch 12 to pivot about pivot pin 13 in response to non-rotational movement of actuator 14 compressing latch spring 11 to remove projection 15 out of engagement with axial groove 52.

With actuator 14 depressed, thereby compressing latch spring 11 and drawing projection 15 into oblong opening 60, guide stop 5 is threaded fully onto the guide base 9 until internal shoulder 72 of guide stop 5 abuttingly engages external shoulder 48 of base 9. Actuator 14 may then be released, thereby allowing latch spring to urge projection 15 against the relatively smooth cylindrical surface 43 of base 9. Guide stop 5 may then be rotated until projection 15 is engaged with axial groove 52, which thereby prevents further rotation of guide base 5. It will be understood that engagement of latch 12 with axial groove 52 prevents further rotation and thus prevents axial displacement of guide stop 5 with respect to guide base 9.

Guide tube 1 is inserted into channels 76 and 56, respectively, until threaded end 30 extends above the second internal shoulder 54 of guide base 9. An insertion tool engages the slot of slotted nut 6 to threadedly advance it over threads 30. Preferably, the threads are coated with a commercially available thread locking compound to fix the slotted nut to the guide tube in the desired position. With slotted nut 6 securely attached, it engages second internal shoulder 54 and prevents removal of guide tube 1 from the assembly. After placement of slotted nut 6, compression spring 10 is placed over threaded end 30 of guide tube 1 and into contact with slotted nut 6. To confine compression spring 10, shoulder washer 7 is placed into the end of guide base 9 with washer 7 in contact with the end of spring 10 opposite slotted nut 6. Spring 10 is now held centered axially within guide base 9. Retaining ring 8 is placed into the end of guide base 9 and is locked into circumferential groove 42. This partially compresses spring 10 and forces guide tube 1 to its fully extended position. In the fully extended position shown in FIG. 1, guide tube tip 26 is substantially aligned with drill bit tip 22.

To complete the assembly in preparation for use, a twist drill bit 3 is placed into the chuck of a drill motor (shown diagrammatically in FIG. 1). End 21 of twist drill bit 3 locks into the chuck of a drill motor hand-piece which constrains the axial movement of the twist drill bit. Twist drill bit 3 is inserted into the open channel of the twist drill guide assembly 20. Twist drill guide assembly 20 is then threadedly coupled to the drill motor housing by internal threads 40, which mate with the corresponding external threads on the drill motor housing 24. Although a threaded coupling with the housing is shown, it is contemplated that the attachment could be made by a snap-fit, bayonet, or other suitable connection mechanism. At this point, the tip 22 of twist drill bit 3 is slightly recessed within the drill guide tube. Moreover, the twist drill bit 3 is supported radially by bearings 2 to inhibit flail of the bit as it rotates at high speeds.

To preset the depth that the twist drill guide bit 3 can be plunged into the work-piece, twist drill guide actuator 14 is depressed and twist drill guide stop 5 is rotated about twist drill guide base 9 until the desired depth is reached. The stop 5 is threaded onto the base 9 so that each revolution of the stop about the base 9 forces the stop 5 to move axially relative to the base 9, a discrete distance equal to the pitch of the thread by which the stop 5 is threaded onto the base 9. The base is etched on its exterior surface with index markings 45 spaced in a predetermined fashion. These index markings provide the user with a legend which visually indicates the number of turns of stop 5 about base 9 from its zero position and therefore the preset depth that drill bit 3 will plunge into the work-piece. Once the desired index marking is adjacent the end of the guide stop 5, actuator 14 may be released and guide stop 5 rotated until the locking mechanism engages axial groove 52. Although in the preferred embodiment the index markings are on the base, it is contemplated that the index marking may be placed on the retractable guide tube. Moreover, guide stop 5 may have an oblong window or series of windows through which markings placed on the base may be viewed by the user.

The twist drill guide tube 1 is now free to move axially within base 9 against the action of compression spring 10 which holds the guide tube 1 in a normally fully extended position. This position prevents accidental contact with moving drill bit 3, thus permitting drill bit 3 to act on a work-piece only when guide tube 1 is withdrawn. In use, the user can visualize tip 22 through sight window 36, thereby permitting the tip 22 to be aligned with the proper position on the work-piece.

When drilling holes for the placement of bone fixation plates the depth of penetration into the underlying bone structure must first be determined. Then the thickness of the fixation plate utilized for purposed of drill hole alignment must be taken into account to precisely set the drill guide depth. The proper depth setting is then dialed into the indexed locking mechanism to the nearest indexed latched position. Thereafter the guide is placed in contact with a properly positioned plate. The surgeon may then utilize sight window 36 to center the drill bit within the pre-drill hole of the fixation plate. In the preferred embodiment, guide tube 1 is pivotal within stop 5 and base 9 such that the user may orient sight window 36 to a desired position. As guide tube 1 is rotated slotted nut 6 slides between second internal shoulder 54 and spring 10. It being understood that the force required to rotate guide tube 1 must overcome the friction between the components which normally holds guide tube 1 in a stationary position. Alternatively, guide tube 1 may be manually pushed into the guide thereby allowing visualization of the drill bit and permitting proper alignment.

Figure 1B:
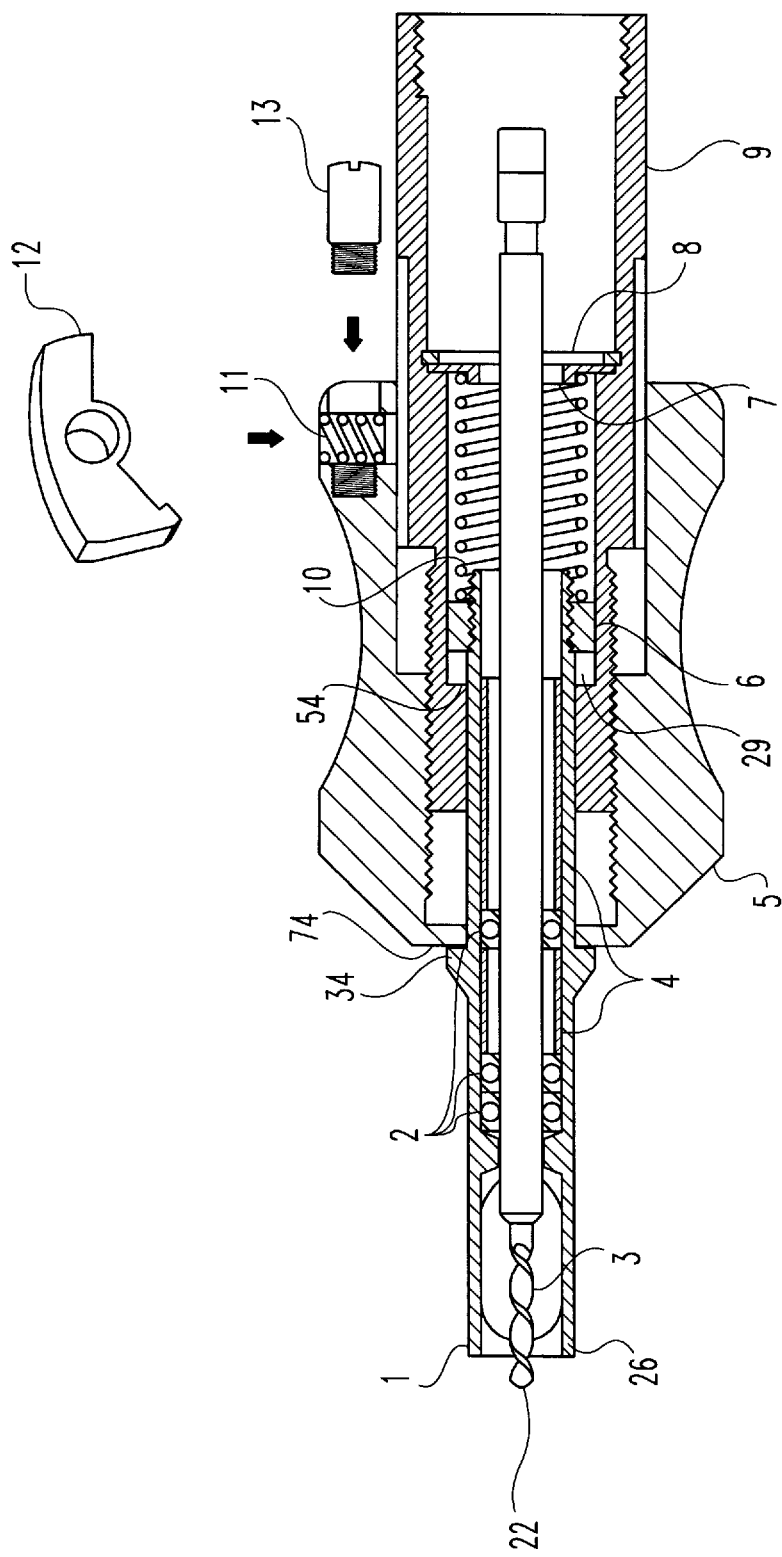
FIG. 1(b) is a cross-sectional view of the adjustable depth drill guide according to the present invention with the drill bit extended from the guide tube.

In use, twist drill guide tube 1 is placed in contact with the work-piece or fixation plate and holding onto the twist drill guide stop 5, the user pushes the twist drill guide against the work-piece. Applying pressure to shoulder 70 forces the drill guide assembly 20 into contact with the work-piece or fixation plate (not shown) and urges drill bit 3 to plunge into the work-piece. Drill bit 3 continues its progression into the work-piece and guide tube 1 continues to slide into base 9 as force applied at shoulder 70 overcomes compression spring 70. This action continues until shoulder 34 on guide tube 1 contacts flange 74 on stop 5 (FIG. 1(b)), thereby preventing further movement of guide tube 1 and further penetration of drill bit 3. As shown in FIG. 1(b), drill bit tip 22 is extended the maximum distance out of guide tube 1 and a corresponding gap 29 has been created between the second internal shoulder 54 of base 9 and slotted nut 6 retained on the guide tube. It will be appreciated that as the maximum drill bit penetration is increased by the adjustment of stop 5 about base 9, gap 29 will increase accordingly.

In the preferred embodiment, the user grasps guide stop 5 about the reduced diameter portion 64. The reduced diameter portion provides the user with a convenient area in which to urge drill bit 3 into the work-piece. In prior devices, primarily because of the small size of the the adjustable stop and the relatively short guide tube, the user is forced to grasp the motor housing. Gripping the drill assembly at a distance spaced from the work-piece increases the difficulty in controlling the drilling procedure. The present design permits the operator, typically a surgeon wearing surgical gloves, to grip the stop adjacent the end of the guiding assembly, thereby allowing greater control over the drilling operation. This can be particularly important in those cases where the surgeon's fingers have already come into contact with bodily fluids, thereby reducing the friction along the outer surface of the guide stop.

Moreover, as can be appreciated by the foregoing description, adjustment of the drill guide mechanism according to the present invention is quite easy to accomplish and provides the surgeon with an exact depth at each indexed locking location. In the preferred embodiment, guide base 9 has only a single axial groove disposed on its external surface 43. In addition, threads 50 are calibrated such that each revolution axially displaces guide stop 5 by one millimeter. Thus, for adjustment of the penetration of twist drill bit 3, the user needs only to depress the indexed latching mechanism actuator 14 to release latch 12 from engagement with axial groove 52 until projection 15 is clear of the axial groove. After a slight rotation of guide stop 5 to clear projection 15 from axial groove 52, actuator 14 may then be released. Further rotation may then be accomplished until latch 12 securely latches into axial groove 52. Thus, in the preferred embodiment the user can be assured that the axial displacement of twist drill bit 3 has been adjusted by exactly one millimeter.

Although the present invention discloses only a single axial groove and the pitch of the threads is calibrated for increments of one millimeter axial displacements, it is contemplated that the outer surface of guide base 9 could have a plurality of axial grooves, thereby increasing the accuracy and the incremental changes provided by the system. Alternatively, or in combination, the calibrated pitch of the threads on stop 5 and base 9 may be modified to provide more or less axial displacement with each revolution. Moreover, although the preferred embodiment utilizes a latch attached to the guide stop and a groove in the base, it is contemplated that the groove may be formed in the stop and the latch attached to the base such that the latch is engagable between the stop and the base.

A further advantage of the adjustable depth drill guide according to the present invention is that the force required to displace latch 12 is normal to the direction of force required to provide axial displacement. Thus, regardless of the pressure applied to urge the drill bit into the work-piece, the latching mechanism will remain securely latched. Moreover, actuator 14 of the indexed latching mechanism, is operable by non-rotational movement. Thus, a rotational force transmitted by the drill bit to the adjustable guide will not act to loosen the latching mechanism. Secure latching of the adjustable guide is particularly important since the drill bit penetration must be accurately set and maintained during many surgical procedures. Any change in the depth of drill bit penetration might cause overpenetration and result in serious injury to the patient.

Figure 9:
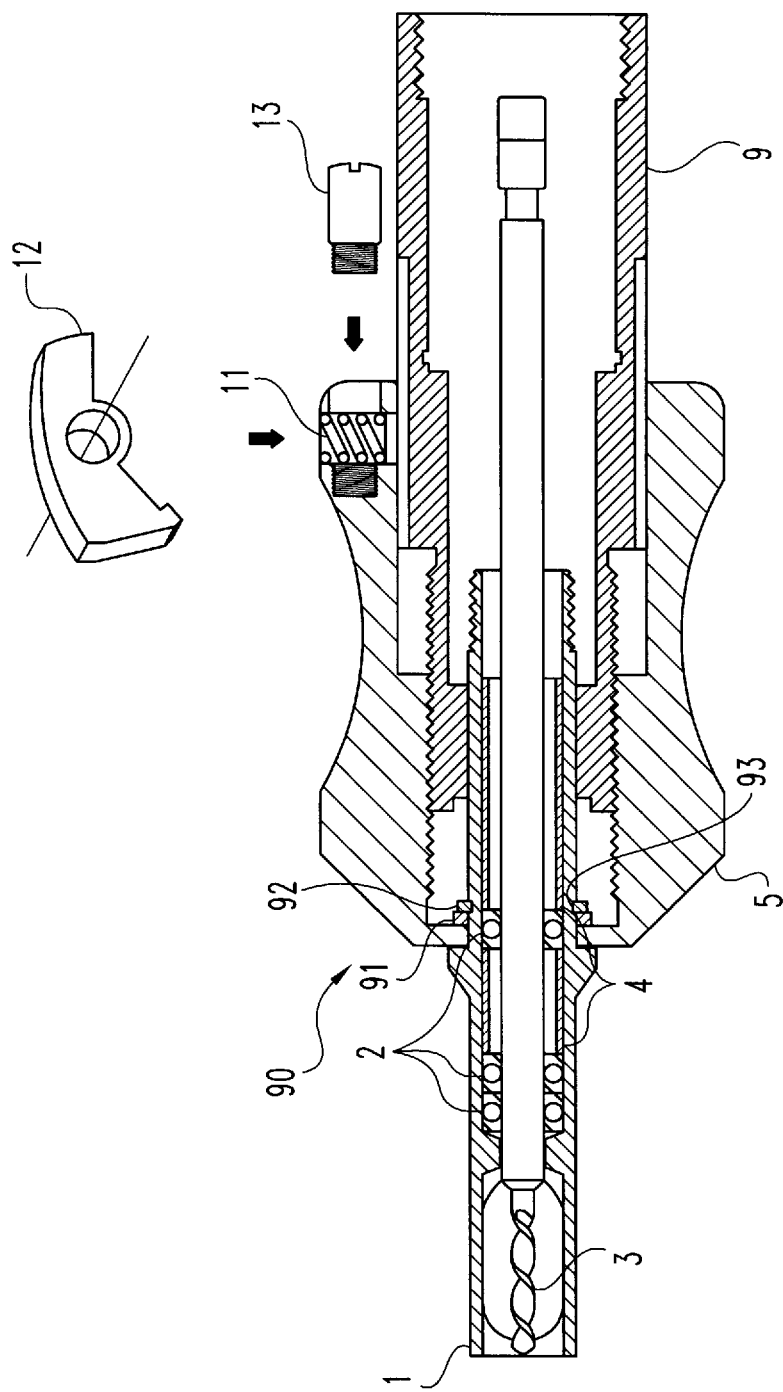
FIG. 9 is a cross-sectional view of an alternative embodiment of an adjustable guide according to the present invention.

Referring now to FIG. 9, an alternative embodiment according to the present invention is shown having guide tube 1 fixedly attached to stop 5. It will be appreciated that in this embodiment, as stop 5 is rotated about base 9, thereby changing the axial displacement, guide tube 1 will likewise move with stop 5 thereby exposing more or less of drill bit 3 depending on the direction of rotation of guide stop 5. Such an embodiment is desirable for use with a drill bit where it is desirable to have the bit exposed at all time. Furthermore, in many cutting operations utilizing burring bits it is preferred that the tip of the guide is in a fixed position permitting the cutting tool to extend a desired distance.

The fixed guide tube adjustable guide 90 comprises most of the same parts utilized for the embodiment shown in FIG. 1. However, guide tube 1 is fixed to stop 5 by a washer 91 and a retaining ring 92 received in recess 93. Similar to the embodiment of FIG. 1, the fixed guide tube adjustable guide is moved from different projection lengths by operation of the indexed latching mechanism. As appreciated from the previous description, this mechanism permits easy and precise adjustment of the penetration depth of the tool.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An adjustable guide for a rotary tool shaft, comprising:
   a base having a first series of threads with a pitch;
   a stop having a second series of threads engaging said first series of threads, wherein rotation of said stop with respect to said base produces an axial displacement proportional to said pitch;
   a latch engageable with said base and said stop, said latch having an actuator controlling said latch between a locked position preventing rotation of said stop with respect to said base and an unlocked position permitting rotation of said stop with respect to said base; and a guide tube having a longitudinal channel adapted to receive a rotary tool shaft, said guide tube received within said stop.

2. The adjustable guide of claim 1, wherein said pitch is selected such that one rotation of said stop axially displaces said stop one unit.

3. The adjustable guide of claim 2, wherein said one unit is one millimeter.

4. The adjustable guide of claim 1, wherein said base includes a series of index markings visually indicating the axial displacement of said stop.

5. The adjustable guide of claim 1, wherein said base includes at least one axial groove and said latch is pivotally attached to said stop, said latch having a projection adapted to engage said at least one axial groove, wherein in said unlatched position said projection is withdrawn from said at least one groove and in said latched position said projection engages said at least one axial groove.

6. The adjustable guide of claim 5, wherein said latch further includes a spring engaging said actuator and normally urging said latch to said latched position.

7. The adjustable guide of claim 1, wherein said guide tube is slidably received within said stop and includes an external shoulder, and further including a biasing spring normally urging said guide tube to a fully extended position, said guide tube reciprocating between a fully extended position with said shoulder spaced from said stop and a fully retracted position with said external shoulder engaging said stop.

8. The adjustable guide of claim 7, wherein said guide tube includes a series of bearings providing axial support for the rotary tool shaft extending therethrough.

9. The adjustable guide of claim 1, wherein said guide tube is fixedly attached to said stop and extends beyond said stop opposite said base.

10. The adjustable guide of claim 1, wherein said latch mechanism is indexed to be engagable only at pre-set intervals, thereby providing a pre-determined axial displacement at each pre-set interval.

11. The adjustable guide of claim 1, wherein said stop includes an outer surface, said outer surface having a shoulder for engagement by a user to urge said stop toward a work-piece.

12. An adjustable guide for a rotary tool shaft, comprising:
a base having a first series of threads having a pitch;
a stop having a second series of threads, said second series of threads threadedly engaging said first series of threads, wherein rotation of said stop about said base produces an axial displacement proportional to said pitch;
an indexed locking mechanism engageable with said stop and said base, said indexed locking mechanism operable by non-rotational movement to lock rotation of said stop about said base at pre-set intervals to thereby produce a pre-determined axial displacement of said stop from said base; and
a guide tube having a longitudinal channel adapted to receive a rotary tool shaft, said guide tube received within said stop.

13. The adjustable guide of claim 12, wherein said base further includes a series of index markings providing visual indication of said axial displacement.

14. An adjustable guide for a rotary tool shaft, comprising:
a base having an external surface defining a series of external threads having a pitch, said external surface defining at least one axial groove;
a stop having an inner surface defining a series of internal threads, said internal threads threadedly engaging said series of external threads, wherein rotation of said stop about said base produces an axial displacement proportional to said pitch;
a latch pivotally attached to said stop, said latch having a projection adapted to engage said groove, wherein engagement of said projection in said axial groove prevents rotation of said stop about said base; and
a guide tube having a longitudinal channel adapted to receive a rotary tool shaft, said guide tube received within said stop.

15. The adjustable guide of claim 14, wherein said stop includes an outer surface and an opening extending from said outer surface to said inner surface, said latch extending through said opening.

16. The adjustable guide of claim 14, wherein said outer surface of said stop includes a shoulder, wherein a user may apply a force against said shoulder thereby urging a rotary tool shaft against a work-piece.

17. The adjustable guide of claim 14, wherein said guide tube further includes a series of bearings adapted to axially support a rotary tool shaft.

18. The adjustable guide of claim 14, wherein said guide tube is fixedly attached to said stop, said guide tube having a distal end disposed opposite said stop, said distal end being substantially flat.

19. The adjustable guide of claim 18, wherein said guide tube includes at least one sight window adjacent said distal tip.

20. The adjustable guide of claim 14, wherein said base further includes index marking for visual indication of said axial displacement between said stop and said base.

21. A method for adjusting a drill guide disposed about a drill bit interconnected with a motorized hand-piece, comprising the steps of:
providing an adjustable depth guide having a base with index markings, a stop threadedly received about the base, and an indexed locking mechanism having an actuator operable by non-rotational movement to prevent rotation between the base and the stop and thereby prevent axial displacement;
positioning the adjustable depth guide over the drill bit;
attaching the base to the motorized hand-piece;
depressing the actuator of the indexed locking mechanism to unlock the locking mechanism;
rotating the stop about the base until the desired index marking is adjacent the stop;
releasing the actuator;
rotating of the stop until the indexed locking mechanism engages and the desired index marking adjacent the stop, thereby setting the guide to stop at a predetermined depth.

22. An adjustable guide, comprising:
a base;
a stop telescopingly engaged with said base, said stop having a aperture;
a guide tube received within said aperture; and
a locking mechanism pivotally attached to said stop and engageable with said base, said locking mechanism having a locked position preventing telescoping movement of said stop with respect to said base and an unlocked position permitting telescoping movement of said stop with respect to said base.

23. An adjustable guide, comprising:

a base;

a stop telescopingly engaged with said base, said stop having an aperture;

a guide tube received within said aperture; and a locking mechanism disposed between said base and said stop, said locking mechanism having an actuator movable to control said locking mechanism between an unlocked position permitting telescoping movement between said base and said stop and a locked position with said locking mechanism engaging said stop and said base to prevent telescoping movement therebetween.

* * * * *